United States Patent [19]

Kelman

[11] Patent Number: 5,084,012
[45] Date of Patent: Jan. 28, 1992

[54] APPARATUS AND METHOD FOR IRRIGATION AND ASPIRATION OF INTERIOR REGIONS OF THE HUMAN EYE

[76] Inventor: Charles D. Kelman, 721 Fifth Ave., New York, N.Y. 10022

[21] Appl. No.: 673,985

[22] Filed: Feb. 22, 1991

[51] Int. Cl.⁵ .............................................. A61M 1/00
[52] U.S. Cl. ......................................... 604/35; 604/28
[58] Field of Search ...................... 604/35, 43, 22, 27, 604/28; 128/3, 4, 5, 6

[56] References Cited

U.S. PATENT DOCUMENTS

| | | | |
|---|---|---|---|
| 2,022,065 | 11/1935 | Wappler | 128/6 X |
| 3,589,363 | 6/1971 | Banko et al. | 604/22 |
| 3,902,495 | 9/1975 | Weiss et al. | 604/22 |
| 4,465,470 | 8/1984 | Kelman | 604/27 |

Primary Examiner—William H. Grieb
Attorney, Agent, or Firm—Darby & Darby

[57] ABSTRACT

An instrument for aspirating and irrigating unwanted material from all regions of the capsule of the eye, especially suitable for cataract removal, including an instrument having a hooked tip portion at the operative end thereof. The hooked tip portion is capable of being deformed into a straightened portion for entering the eye. The straightened portion resiliently returning to its hooked configuration upon release of an outside force, whereby the hooked tip portion is capable of access to inner peripheral regions of the posterior capsule which previously were accessible only with great difficulty. The instrument is capable of supplying treatment fluid to the region of the eye in question for irrigating the region and the instrument is capable of aspirating the region for removal of fluid and unwanted tissue.

12 Claims, 2 Drawing Sheets

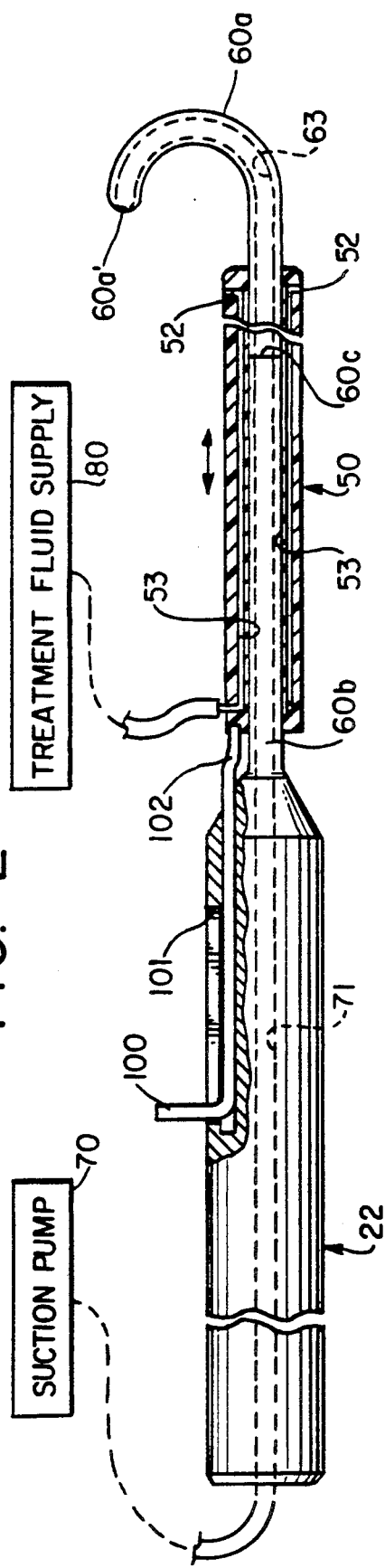
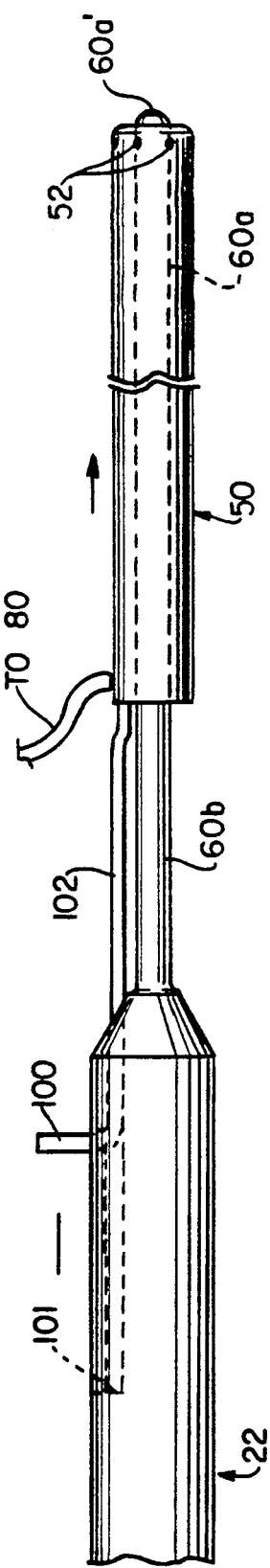

APPARATUS AND METHOD FOR IRRIGATION AND ASPIRATION OF INTERIOR REGIONS OF THE HUMAN EYE

BACKGROUND OF THE INVENTION

The present invention relates to material removal devices, and, more particularly, to an irrigation and aspiration instrument having a selectively hooked or straight portion at the operative end thereof for irrigating and aspirating material from relatively inaccessible places. Although by no means limited thereto, the present apparatus is of particular advantage when employed in surgical procedures for removing material from the capsular bag of the eye.

Conventional vibratory instruments for the removal of material from the eye have used a handpiece having a straight operative tip at the end thereof. U.S. Pat. No. 3,589,363, which is incorporated herein by reference, involves an instrument having a handpiece which has an elongated tip at one end. The elongated tip is inserted through an incision made in the cornea. The instrument is capable of vibrating the operative tip at ultrasonic frequencies of variable amplitude and duration to break apart particles of the material, such as a cataracted lens, to be removed.

A source of fluid and a source of fluid suction are provided at the operative end of the instrument, respectively, to dispense and withdraw fluid to and from the area in proximity of the material to be removed.

FIG. 1 illustrates the conventional solution to removing material from the eye. The opaque lens or cataract to be removed is designated as 10 and is encased in a membrane or capsular bag 12, including a front portion closest to the cornea, known as the anterior capsule 12a, and rear portion, known as the posterior capsule 12b.

Typically, a small incision 14 is made in the cornea 16 as far as possible from the center of the pupil area. The central portion of the anterior wall is opened up for access and instrument such as that described in U.S. Pat. No. 3,589,363 is used to fragment the cataracted lens and to aspirate the fragments from the accessible regions of the capsular bag such instrument has an elongated straight tip 20, seen in FIG. 1, capable of supporting ultrasonic vibrations. In this arrangement, particularly if the anterior wall opening is relatively small, only the central region of the interior of the capsular bag 12 is readily accessible to the tip, since the amount of manipulation by manually moving the handpiece 22 within the capsular bag 12 is relatively limited by the straight tip being confined at two locations along its length, namely, by the small incision in the cornea and also by the remaining peripheral portions of the anterior wall of the capsule.

For example, the handpiece 22 can be moved at angles $A_1$, $A_2$, $A_3$ and $A_4$ to enable the elongated straight tip 20 to reach different portions in the central region of the capsule. However, the capsule portions at the periphery of the capsular bag are not readily accessible to the elongated straight tip 20 because the size of the incision and the remaining anterior wall of the capsule 12 restrict the movement of the elongated straight tip 20. Therefore, the elongated tip 20 can not easily be moved to angles which would enable it to reach the interior peripheral portion of the capsule 12. Thus, it is very difficult for the surgeon using the conventional instrument to manipulate it so as to remove material, e.g. fragments of the cataracted lens, which is located at the inner peripheral regions of the anterior capsule 12.

SUMMARY OF THE INVENTION

This invention is directed to a material removal apparatus in which problems with the prior art devices are eliminated. It is, therefore, a general object of the invention to provide an apparatus capable of removing material from tissue of an enclosed area. More specifically, it is an object of the present invention to provide a working instrument to aspirate and irrigate all regions of the posterior capsule of the eye even though the peripheral portions or the anterior wall of the capsule remain intact.

Another object of the present invention is to provide a surgical instrument having an operative tip capable of being selectively transformed from a straight tip to a hooked tip, whereby material to be removed, which is located in the peripheral interior region of the capsule, can be withdrawn.

In accordance with this invention, an irrigation and aspiration surgical instrument is provided with an elongated tube having a resiliently deformable tip portion. The tip portion has a hooked shape in a relaxed condition. A sleeve means, as for example a tubular sleeve, is slidably movable onto the tip portion, to straighten the hooked tip portion into a straightened condition, and off the tip portion to allow the latter to again assume its relaxed hooked configuration. When the tip is in a straightened condition the tube may be readily inserted into the incision in the cornea and into the capsular bag. The tip, in straightened condition, ay be manipulated by moving the handpiece to reach regions of the capsular bag across from the region at which the tip entered the eye. The tip resiliently returns to its relaxed hooked shape upon moving the tubular sleeve off the straightened tip end portion and back along the tube. With the tip in a hooked shape, it may extend to and be used in the inner peripheral regions of the capsular bag. Thus, those regions may also be aspirated to remove tissue and fluid there from.

Other objects and advantageous features of this invention will be apparent from the following description of the preferred embodiment with reference to the accompanying drawings.

BRIEF DESCRIPTION OF THE DRAWINGS

FIG. 2 is a partly schematic, partly sectional, view of the instrument according to the present invention showing the tip in relaxed, hooked condition.

FIG. 3 is a partly schematic, partly sectional, view of the instrument according to the present invention showing the tip in straightened condition.

DETAILED DESCRIPTION OF THE DRAWINGS

Figure 1:
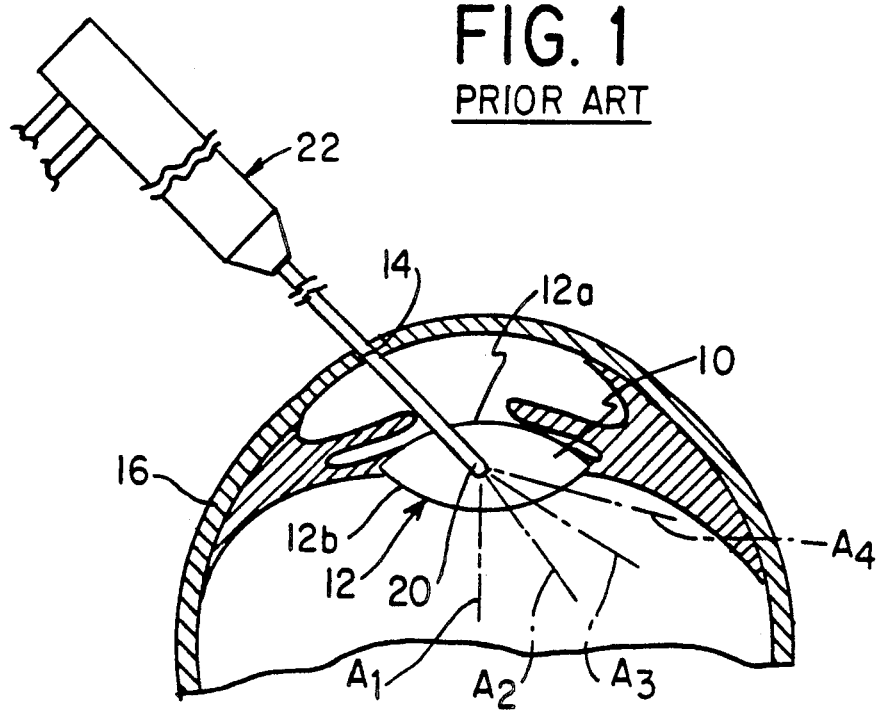
FIG. 1 is a pictorial representation of a conventional instrument showing the use in cataract removal.

In the ensuing detailed description, the invention will be described in terms of its use as a surgical instrument, particularly as applied to cataract removal. However, it will be understood that the principles of the invention are not so limited, and the apparatus described may be capable of other applications.

Referring to FIG. 2, a schematic diagram of a preferred embodiment of the instrument for irrigating and aspirating a material is illustrated.

A tube 60 is formed of a straight shank portion 60b at the end thereof which is connected to a handpiece 22. At the other, or operative, end of the tube 60, is a tip portion 60a. Tip portion 60a is resiliently deformable from a hooked shape into a straight shape. Preferably, in hooked shape, the tip portion 60a may have a bend of up to about 180 degrees. It will be appreciated that the hooked portion may be formed to bend in varying angles up to about 180 degrees.

The tube 60, preferably, has an outer diameter of no more than approximately 1 mm and has a conduit 63 extending through the length of the tube to opening 60a'. Tube 60 is connected, through the handpiece 22, to a source of vacuum 70, for aspirating material through opening 60a'. For this purpose, the source of vacuum 70 may be of the type shown in U.S. Pat. No. 3,589,363 formed as a vacuum pump.

Preferably, the tip portion 60a is formed of a resilient material, such as polypropylene or other plastic material. The resilient material may be deformed upon the application of an outside force, as is described in detail below. Further, the resilient material of the tip portion 60a has a memory (meaning that the tube portion 60a, forming the operative tip of the instrument, is made of a material which will return to its natural predetermined hooked shape after externally applied straightening force is removed).

The free end of the tip portion 60a may be of rounded shape to avoid injury to the tissue when the tip is inserted into the eye through incisions made in the cornea and in the anterior wall capsule.

In the preferred embodiment, a tubular sleeve 50 forms a hollow cylinder around the tube 60 for housing a portion of the tube 60. The tubular sleeve 50 has an inner diameter which is only slightly larger than the outer diameter of the tube 60 so that sleeve 50 will slide along tube 60. The tubular sleeve 50 is formed of a rigid material. It will be appreciated that the rigid material of the sleeve can be metal, TEFLON, or other plastic materials, as are known in the art and suitable for use in surgical procedures of the eye.

The tubular sleeve 50 may be slid longitudinally along the tube 60 and selectively moved onto and off the flexible tip portion 60a. As the tubular sleeve 50 is slid onto the tip portion 60a, the sleeve acts as an outside force to press against the natural bend of the hooked portion, whereby the bend in the hook tip portion 60a is straightened. As illustrated in FIG. 3, once the tubular sleeve is moved over and surrounds the hooked tip portion 60a, the hooked portion 60a is deformed and becomes a straight tip.

In a preferred embodiment, the sleeve 50 has irrigating openings 52 provided at the end thereof nearest the operative end of the instrument and a conduit extending through the sleeve. A source of irrigating fluid 80, such as saline solution or medicated solution, can be pumped to the irrigating openings 52, via a conduit 53 in the sleeve, so as to be delivered to the area to be irrigated. In an alternative embodiment (not shown), the source of irrigating fluid 80 may be supplied to the handpiece 22 and through a conduit in the tube 60 to the operative end of the instrument.

A control arm 100 may be provided in the handpiece 22 for controlling the sliding of the tubular sleeve 50 along the tube 60. When the control arm (FIG. 2) is pushed forwardly in its slot 101, the connecting portion 102 causes the tubular sleeve 50 to move in a direction from the straight shank portion 60b of tube 60 to the tip portion 60a. Thereby the tubular sleeve 50 can be moved onto the hooked portion 60a for deforming the hooked portion as described above. Retracting arm 100 moves the tubular sleeve 50 in a direction from the hooked tip portion 60a to the straight shank portion 60b of the tube so that the tubular sleeve 50 is moved off the hooked portion 60a.

Figure 4:
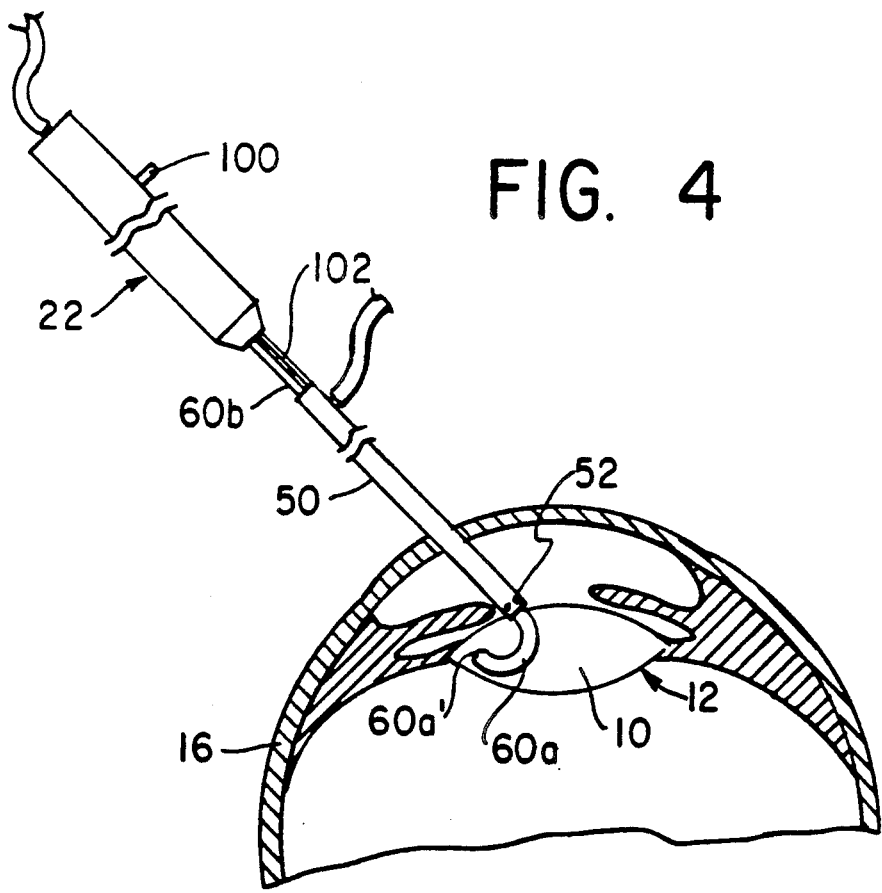
FIG. 4 is a pictorial representation of an instrument according to the present invention showing the use in removal of material from inner peripheral regions of the capsular bag.

When the tubular sleeve portion 50 is moved over the hooked portion 60a it straightens out the hooked portion, as shown in FIG. 3. In this configuration, the tip portion of the tube 60a may be easily inserted through the small incision 14 in the cornea and into the posterior capsule 12, as shown in FIG. 4. The incision need only be about 1 to 3 mm in length to provide proper access for the operative end of the tube with the tip portion 60a in straight-tip condition i.e. surrounded by sleeve 50. As is known in the art, a small aperture may be surgically made in the anterior wall of capsule 12. The operative end of the tube 60 may be directed by manipulating the handpiece 22 so that the tip 60a, with the sleeve 50 over it, may reach the central regions of the posterior capsule 12b. Afterwards, the sleeve 50 may be retracted off the portion 60a onto the straight shank portion 60b of tube 60 as illustrated in FIG. 2, whereby the tip portion 60a again automatically—because of the memory of the material of portion 60a—assumes the hooked configuration of predetermined angle. It will be seen that in this configuration the operative end of the hooked tip portion 60a will extend around the remaining peripheral portions of the anterior wall of the capsule and reach into the otherwise inaccessible interior peripheral regions of the capsule as shown in FIG. 4. Thus, in this configuration the handpiece 22 may be manipulated to direct the operative end of the hooked tip portion 60a around to the different peripheral inner regions of the capsule 12a.

The separated unwanted tissue and excess treatment fluid may be aspirated with suction pump 70 through conduit 71 in the tube 60. Upon removing the unwanted tissue and fluid, the tubular sleeve 50 may again be moved onto the tip portion 60a so that the hook shape will be straightened out and the instrument may be easily withdrawn from the eye.

In a preferred embodiment the tube portion 60b is of rigid construction, preferably polymethylmethacrylate and extends from the end at which tube 60 is fixed to the handpiece 22, to a region 60c which is located within the confines of sleeve 50 in all positions of sleeve 50 on tube 60. Tip portion 60a which is preferably preshaped (into hooked configuration) polypropylene is integrally connected to portion 60b at 60c.

The specification and drawings are set forth by way of illustration and not limitation, and various modifications may be made therein without departing from the spirit of the invention which is to be limited solely by the scope of the claims.

I claim:

1. A surgical instrument for aspirating and irrigating material at substantially all interior regions of the posterior capsule of an eye in which at least peripheral portions of the anterior wall of the capsule remain intact, comprising;

a hollow tube member;

said hollow tube member having an elongated resiliently deformable tip portion with a fluid conduit extending therethrough to the region of the tip thereof, said tip portion being deformable from a relaxed hooked condition in which said tip portion has a hooked shape into a deformed condition in which said tip portion is straight;

a sleeve member surrounding and being reciprocally slidable longitudinally on said tube for deforming and thereby straightening said tip portion thereof when the latter is in said relaxed hooked condition for insertion into the eye;

said tip portion comprising a material having a memory for resiliently returning to said relaxed hooked condition thereof in response to said sleeve member being moved along said tube away from said tip portion thereof;

means in one of said members for supplying an irrigation fluid to the region of the capsule to be aspirated; and fluid suction means in said tip portion for aspirating fluid from the interior of the capsule.

2. The apparatus of claim 1 further comprising control means for selectively controlling the position of said sleeve on said tube.

3. The apparatus of claim 1 wherein said tip portion, in hooked configuration thereof, has a bend of about 180 degrees.

4. The apparatus of claim 1 wherein said means for supplying an irrigation fluid is coupled to said tip portion of said tube member.

5. The apparatus of claim 1 further comprising a elongated handpiece having an end operatively connected to said tube member at the end of said tube spaced from said flexible tip portion.

6. The apparatus of claim 5 wherein said tube member has a more flexible portion at the tip end thereof and a more rigid portion at the opposite end thereof connected to said handpiece.

7. The apparatus of claim 6 wherein said more flexible portion is polypropylene and said more rigid portion is polymethylmethacrylate.

8. The apparatus of claim 5 further comprising a control means on said handpiece, said control means operatively connected to said sleeve for sliding said sleeve member onto and off said flexible tip portion in response to operation of said control means.

9. The apparatus of claim 1 wherein said sleeve member is tubular and is formed of relatively rigid plastic material.

10. The apparatus of claim 9 wherein said tubular sleeve is formed of polymethylmethacrylate.

11. A method for aspirating and irrigating tissue at substantially all interior regions of the posterior capsule of an eye in which at least peripheral portions of the anterior wall of the capsule remain intact comprising the steps of:

providing an instrument having a hollow tube having a resiliently deformable tip portion deforming the tip portion from a relaxed condition in which the tip portion has a hooked shape, to a deformed condition in which the tip portion is straight by sliding a tubular sleeve onto the tip portion;

inserting the tip portion and sleeve in said straight deformed condition of the tip portion, thru an incision in the cornea and into the posterior capsule;

sliding the tubular sleeve back from the tip portion so as to allow the tip portion to resiliently return to its relaxed condition, the tip portion including a material having a memory for returning it to its relaxed condition;

supplying irrigation fluid to the region of the capsule to be aspirated through the sleeve portion; and aspirating fluid from the interior of the capsule through the tip portion.

12. The method of claim 11 wherein the step of sliding the sleeve includes operating a control member for sliding the tubular sleeve on the hollow tube.

* * * * *